US006482165B1

(12) United States Patent
Patton et al.

(10) Patent No.: US 6,482,165 B1
(45) Date of Patent: *Nov. 19, 2002

(54) HOMEKIT FOR DETERMINING ATTENTION DEFICIT HYPERACTIVITY DISORDER

(75) Inventors: David L. Patton, Webster, NY (US); Richard N. Blazey, Penfield, NY (US); Peter A. Parks, Topeka, KS (US)

(73) Assignee: Eastman Kodak Company, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/692,682

(22) Filed: Oct. 19, 2000

Related U.S. Application Data

(63) Continuation of application No. 09/597,610, filed on Jun. 20, 2000.

(51) Int. Cl.[7] ............................................. A61B 5/00
(52) U.S. Cl. ..................................... 600/549; 600/300
(58) Field of Search ........................... 600/26–28, 300, 600/549, 558; 128/897, 898

(56) References Cited

U.S. PATENT DOCUMENTS

| | | | | |
|---|---|---|---|---|
| 4,920,973 A | * | 5/1990 | Tanaka et al. | 600/549 |
| 5,365,939 A | * | 11/1994 | Ochs | 600/545 |
| 5,377,100 A | | 12/1994 | Pope et al. | 600/545 |
| 5,725,472 A | * | 3/1998 | Weathers | 600/21 |
| 5,913,310 A | | 6/1999 | Brown | 128/897 |
| 5,947,908 A | * | 9/1999 | Morris | 600/484 |
| 5,995,857 A | * | 11/1999 | Toomim et al. | 600/322 |
| 6,117,075 A | * | 9/2000 | Barnea | 600/300 |
| 6,238,354 B1 | * | 5/2001 | Alvarez | 600/549 |

OTHER PUBLICATIONS

Nature Magazine, Apr. 2000, vol. 6, No. 4, pp 470–473, Functional deficits in basal ganglia of children with attention-deficit/hyperactivity disorder shown with functional magnetic resonance imaging relaxometry, by Martin H. Treicher, Carl M. Anderson, Ann Polcari, Carol A. Glod, Luis C. Maas and Perry F. Renshaw.

Biofeedback and Self-Regulation, vol. 16, No. 3, 1991, Research Recognition Award paper, Disclosure on the Development of EEG Diagnostics and Biofeedback for Attention-Deficit/Hyperactivity Disorders, by Joel F. Lubar, University of Tennessee.

Biofeedback and Self-Regulation, vol. 20, No. 4, 1995, Spectral Characteristics of Skin Temperature Indicate Peripheral Stress-Response, by Vladimir Shusterman and Ofer Barnea, Tel Aviv University.

U.S. patent application Ser. No. 09/597,610, filed on Jul. 20, 2000, by Richard N. Blazey, Peter A. Parks, David L. Patton.

* cited by examiner

Primary Examiner—Kevin Shaver
Assistant Examiner—Charles Marmor, II
(74) Attorney, Agent, or Firm—William F. Noval

(57) ABSTRACT

A kit and method for determining whether an individual has Attention Deficit Hyperactivity Disorder, comprising a device for sampling the peripheral skin temperature of a human subject during a predetermined time interval when the subject is in an inactive state, and an analyzer for analyzing the sampled peripheral skin temperature data for a pre-selected parameter, to determine whether the pre-selected parameter has a value indicative of ADHD.

17 Claims, 9 Drawing Sheets

| DATE | TIME | | |
|---|---|---|---|
| 6/13/00 | 8:00 AM | 2.8 | 0.65 |
| 6/13/00 | 12:00 NOON | 2.7 | 0.67 |
| 6/13/00 | 5:00 PM | 3.1 | 0.65 |
| 6/14/00 | 8:00 AM | 2.9 | 0.65 |
| 6/14/00 | 12:00 NOON | 2.8 | 0.66 |
| 6/14/00 | 5:00 PM | 3.0 | 0.68 |

HOMEKIT FOR DETERMINING ATTENTION DEFICIT HYPERACTIVITY DISORDER

CROSS REFERENCE TO RELATED APPLICATIONS

This patent application is a continuation of the earlier filing date of U.S. patent application Ser. No. 09/597,610, filed Jun. 20, 2000.

FIELD OF THE INVENTION

This invention relates in general to a technique for diagnosing Attention Deficit Hyperactivity Disorder (ADHD) and more particularly to a home kit technique for measuring an individual's peripheral temperature to determine values indicative of ADHD.

BACKGROUND OF THE INVENTION

ADHD is the most common neurobehavioral disorder of childhood as well as among the most prevalent health conditions affecting school-aged children. Between 4% and 12% of school age children (several millions) are affected. $3 billion is spent annually on behalf of students with ADHD. Moreover, in the general population, 9.2% of males and 2.9% of females are found to have behavior consistent with ADHD. Upwards of 10 million adults may be affected.

ADHD is a difficult disorder to diagnose. The core symptoms of ADHD in children include inattention, hyperactivity, and impulsivity. ADHD children may experience significant functional problems, such as school difficulties, academic underachievement, poor relationships with family and peers, and low self-esteem. Adults with ADHD often have a history of losing jobs, impulsive actions, substance abuse, and broken marriages. ADHD often goes undiagnosed if not caught at an early age and affects many adults who may not be aware of the condition. ADHD has many look-alike causes (family situations, motivations) and co-morbid conditions (depression, anxiety, learning disabilities).

Diagnosis of ADHD involves a process of elimination using written and verbal tests. However, there is no one objective, independent valid test for ADHD. Various objective techniques have been proposed but have not yet attained acceptance. These include:

1. The eye problem called convergence insufficiency was found to be three times more common in children with ADHD than in other children by University of California, San Diego researchers.
2. Infrared tracking to measure difficult-to-detect movements of children during attention tests combined with functional MRI imaging of the brain were used by psychiatrists at McLean Hospital in Belmont, Mass. to diagnose ADHD in a small group of children (*Nature Medicine*, Vol. 6, No. 4, April 2000, Pages 470–473).
3. Techniques based on EEG biofeedback for the diagnoses and treatment of ADHD are described by Lubar (*Biofeedback and Self-Regulation*, Vol. 16, No. 3, 1991, Pages 201–225).
4. U.S. Pat. No. 5,913,310, issued Jun. 22, 1999, inventor Brown, discloses a video game for the diagnosis and treatment of ADHD.
5. U.S. Pat. No. 5,377,100, issued Dec. 27, 1994, inventors Pope et al., discloses a method of using a video game coupled with brain wave detection to treat patients with ADHD.
6. Dr. Albert Rizzo of the Integrated Media Systems Center of the University of Southern California has used Virtual Reality techniques for the detection and treatment of ADHD.

Although skin temperature spectral characteristics have been shown to indicate stress-related changes of peripheral vasomotor activity in normal subjects, there has been no disclosure of use of variations in skin-temperature response to assist in diagnosing ADHD. (See: *Biofeedback and Self-Regulation*, Vol. 20, No. 4, 1995).

As discussed above, the primary method for diagnosing ADD is the use of a bank of written and verbal tests designed to assess criteria established by American Medical Association (AMA) as described in the Diagnostic and Statistics manual-IV (DSM-IV) and administered by the school psychologist or other licensed practitioner. In some cases those individuals who meet DSM-IV criteria for ADHD diagnosis are prescribed a drug such as Ritalin. Behavioral observations of the patient while on Ritalin are conducted to assess the imact of prescribed medication. U.S. patent application (Ser. No. 09/597,610) describes an apparatus and method of determining whether an individual has Attention Deficit Disorder. In none of the prior art is there disclosed a method for screening for ADHD at home using a home kit.

There is thus a need for a simple, inexpensive, and reliable technique for determining whether an individual has Attention Deficit Hyperactivity Disorder (ADHD) in the home.

SUMMARY OF THE INVENTION

According to the present invention, there is provided a solution to the problems and fulfillment of the needs discussed above.

According to a feature of the present invention, there is provided a kit for determining whether an individual has Attention Deficit Hyperactivity Disorder (ADHD) comprising:

a device for sampling the peripheral skin temperature of a human subject during a predetermined time interval when the subject is in an inactive state; and an analyzer for analyzing the sampled peripheral skin temperature data for a pre-selected parameter, to determine whether said pre-selected parameter has a value indicative of ADHD.

ADVANTAGEOUS EFFECT OF THE INVENTION

The invention has the following advantages.

1. A device and technique for diagnosing ADHD is provided which is simple, inexpensive and reliable and usable in the home in the form of a kit.

DETAILED DESCRIPTION OF THE INVENTION

According to the invention, it has been found that a signature of ADHD is hidden in fluctuation of the temperature of the skin as measured at the extremities such as at a fingertip. Biofeedback practitioners have long used measurement of hand temperature to help subjects manage their physiology by controlling blood flow to the extremities. The literature reports that reduced blood flow to the brain is frequently found in patients with ADHD.

Figure 1:
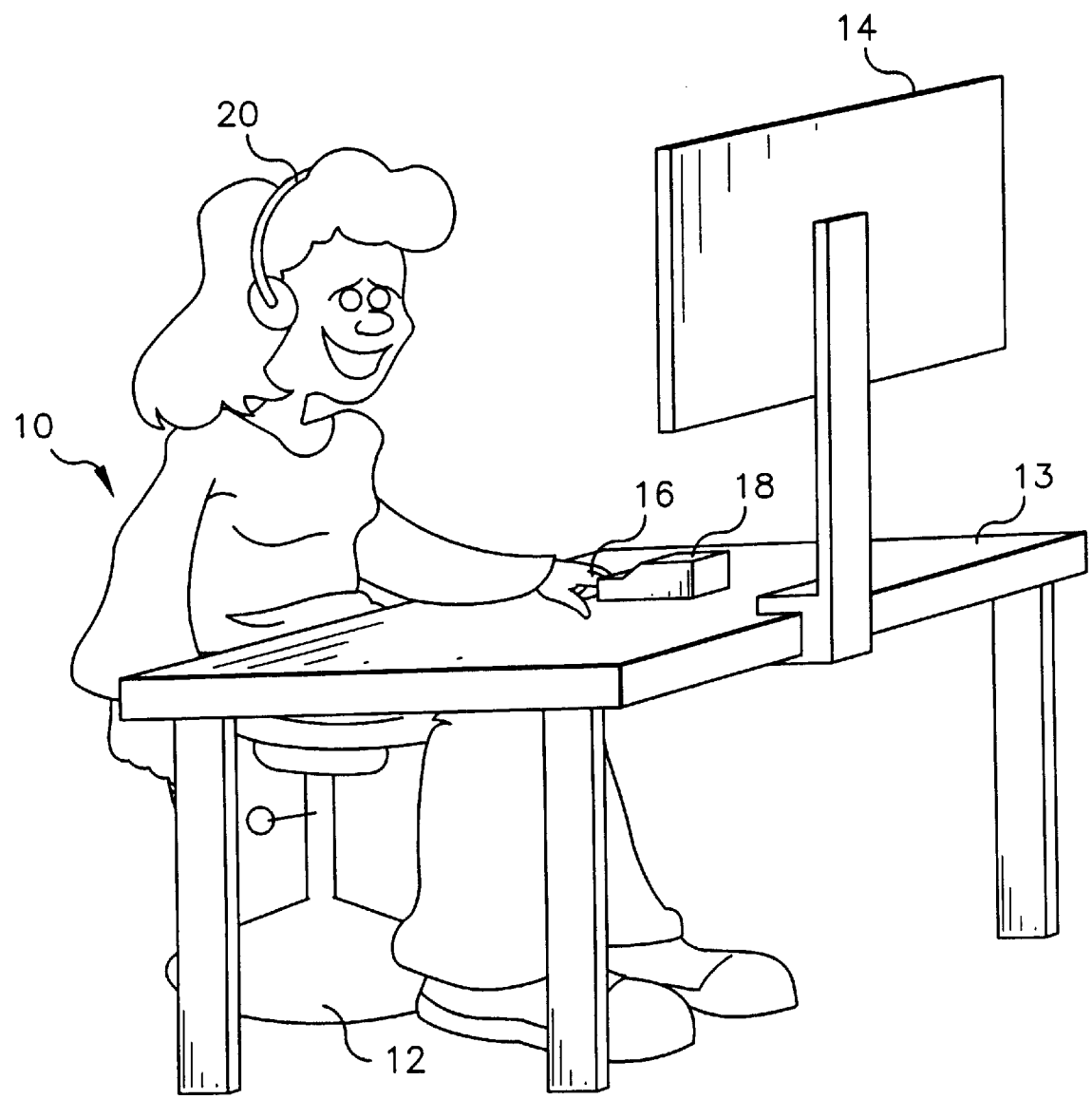
FIG. 1 is a diagrammatic view illustrating use of an embodiment of the present invention.
Figure 2:
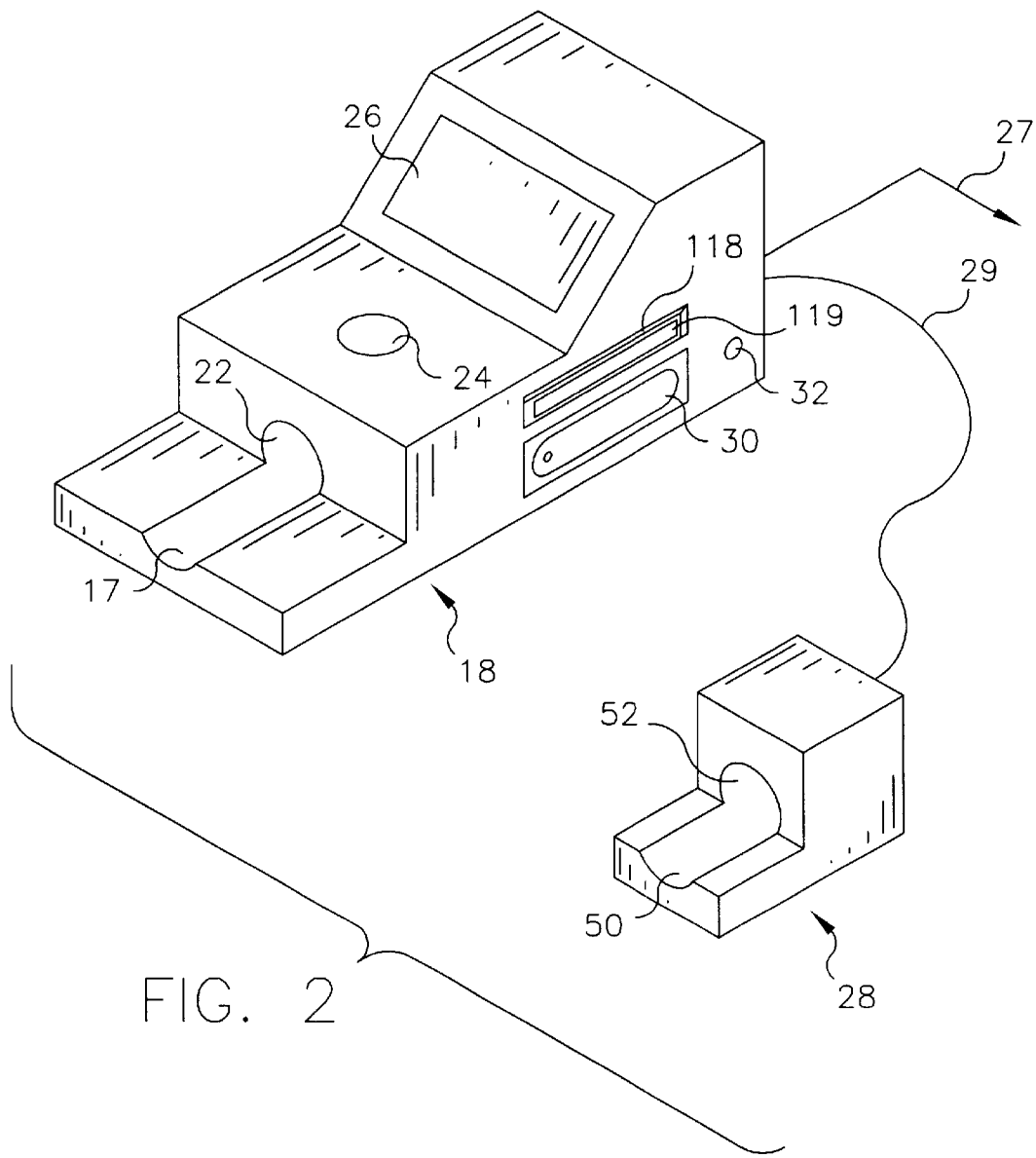
FIG. 2 is a perspective view showing in greater detail the embodiment of FIG. 1.

As shown in FIG. 1, a subject 10 is sitting on a chair 12 at a table 13 watching a screen 14. The screen 14 is used to block any visual stimulus from disturbing the subject 10. The subject 10 is wearing a set of earphones 20. The earphones 20 can be connected to a sound-generating device not shown. The earphones 20 can be used to block out ambient noise or to produce a white noise intended to reduce or eliminate the audio stimulus from the environment during the test. The subject is at rest in an inactive state. The fingertip 16 of subject 10 is inserted into an analyzer module 18, where the skin temperature is measured via a sensor 22 (shown in FIG. 2).

Analyzer module 18 includes a temperature sensor 22, where the subject 10 inserts their fingertip 16 in groove 17, an on/off switch 24, and a display 26. The analyzer module 18 can have an internal power supply, such as a battery 30, or an external low voltage power supply port 32 for an external low voltage power supply (not shown), such as used for a telephone. The analyzer module 18 can be connected to an external CPU 44 (shown in FIG. 10) via a cable 27 (such as an USB or RS 232 cable), or wireless transmitting device such as an RF or IR link (not shown). In a further embodiment a second temperature sensor module 28 can be connected to the analyzer 18 via a cable 29. The second temperature sensor module 28 can be used to sample the skin temperature of the subject's 10 other hand and includes groove 50 and temperature sensor 52.

Figure 3:
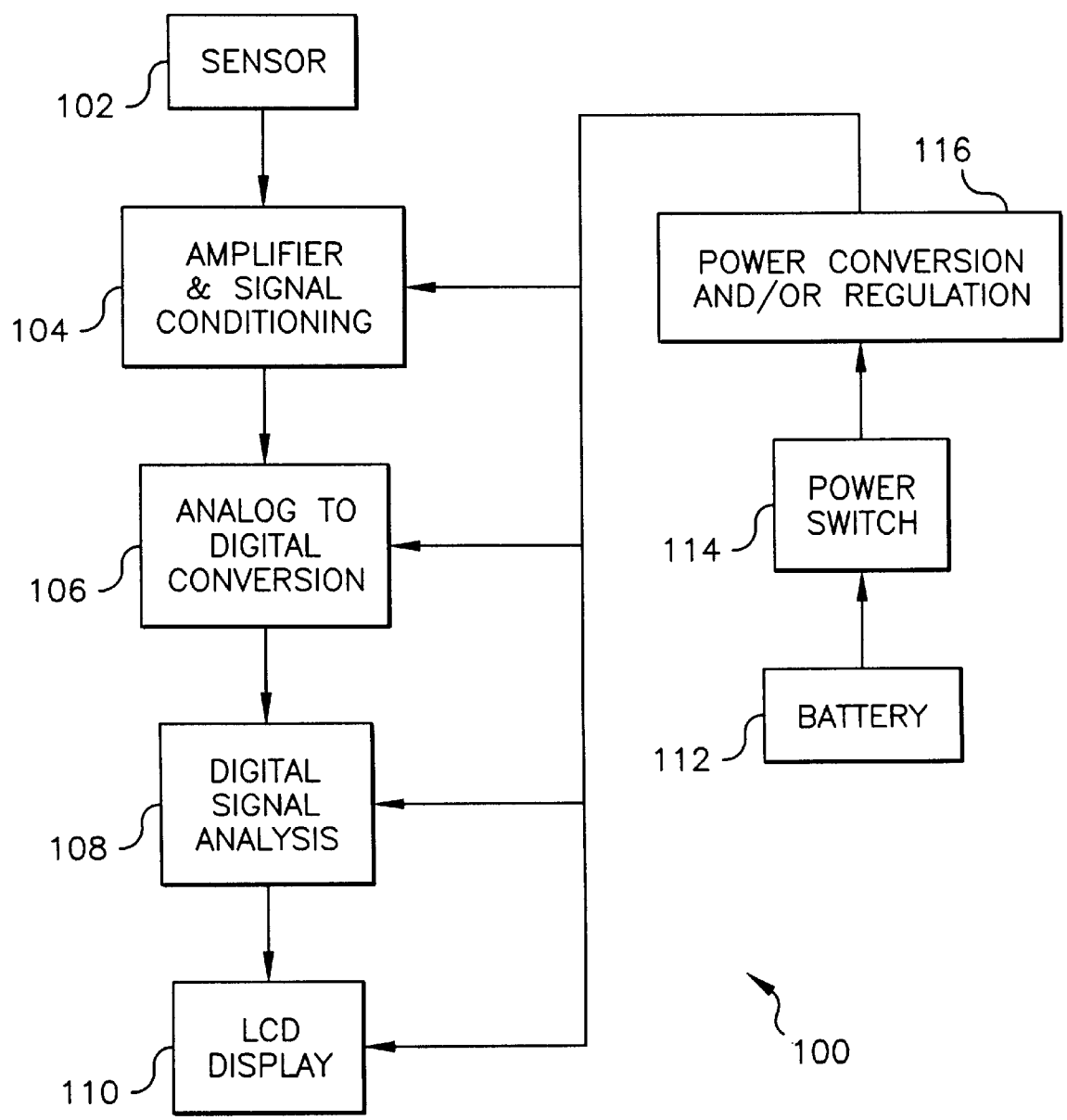
FIG. 3 is a block diagram of a system incorporating the present invention.

Referring now to FIG. 3, analyzer module 18 includes analyzer circuit 100 including temperature sensor 102, temperature sampling, amplifier and signal conditioner circuit 104, analog to digital converter 106, digital signal analysis 108, LCD (fluid crystal display) display 110, battery 112, power switch 114 and power conversion and/or regulation 116.

Figure 4:
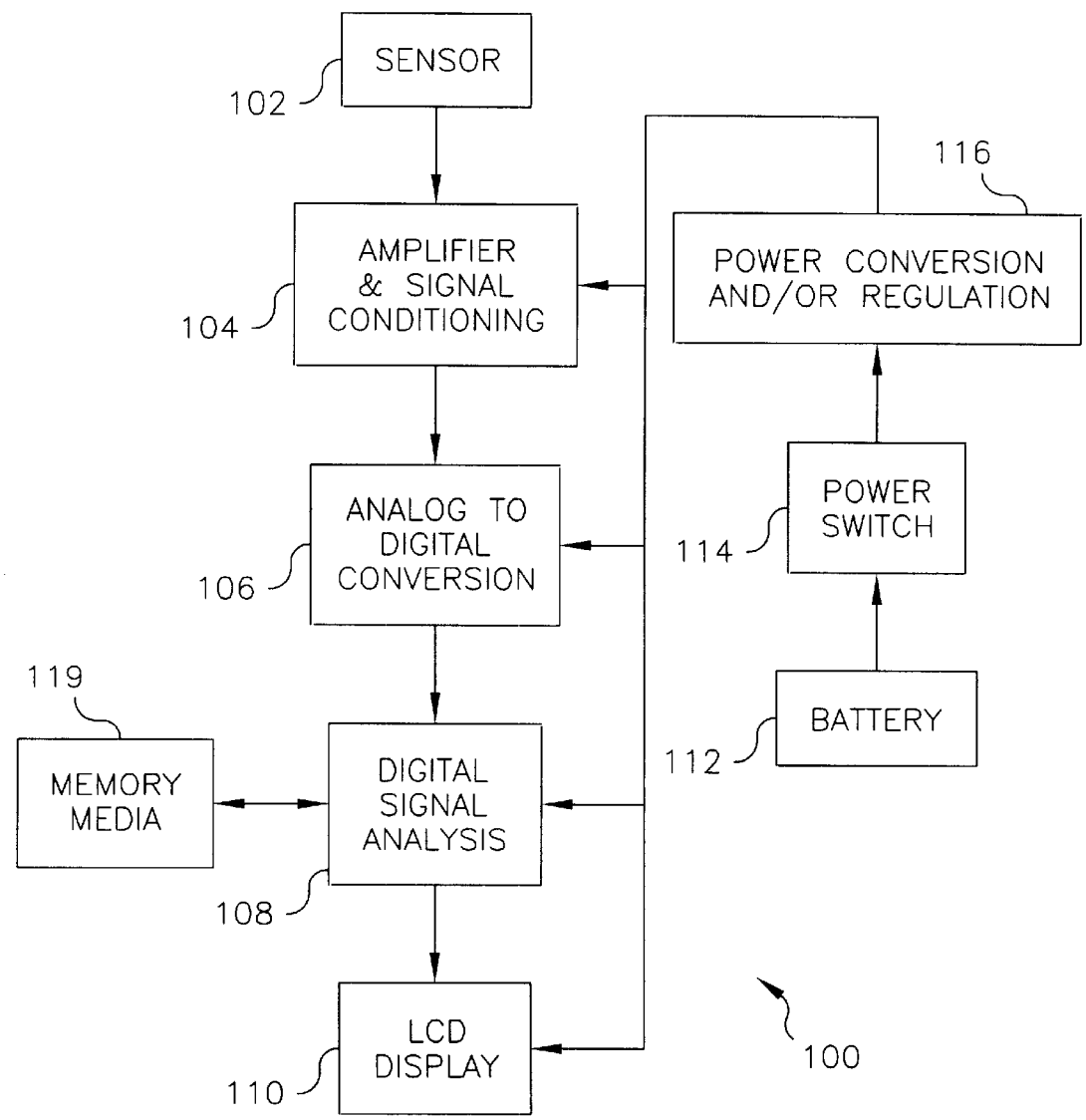
FIG. 4 is a block diagram of a modification of the system of FIG. 3.

FIG. 4 shows a modification of the circuit 100 of FIG. 3 and includes a slot 118 for receiving a memory media 119 (such as a memory card, floppy disk, etc.) which can provide system upgradability and removable data export without compromising safety isolation.

Referring again to FIG. 1, the fingertip temperature is first recorded during an interval when the subject 10 has been asked to sit quietly for a given period of time, nominally about 10 minutes. The time period may be shorter or longer. The temperature data is sampled via circuit 104 (shown in FIG. 3) at a time interval $\Delta t$ creating a list of N temperature samples, which are digitized by A/D converter 106 and which are stored in memory (not shown). The N samples are divided into windows of m samples. The data from each window is then passed through a Fast Fourier Transform (FFT) algorithm in data signal analysis circuit 108 producing $2^{m-1}$ data points spaced equally in frequency space. The values are complex numbers having form $$FFT(f_n) = A(f_n) + B(f_n)i$$

where i is the $\sqrt{-1}$. The Phase $\Phi(f_n)$ can be found from the equation $$\Phi(f_n) = \text{Tan}^{-1}\left(\frac{B(f_n)}{A(f_n)}\right) \quad (.00)$$

and the Magnitude $M(f_n)$ from $$M(f_n) = \sqrt{B(f_n)^2 + A(f_n)^2} \quad (0.0)$$

Figure 5:
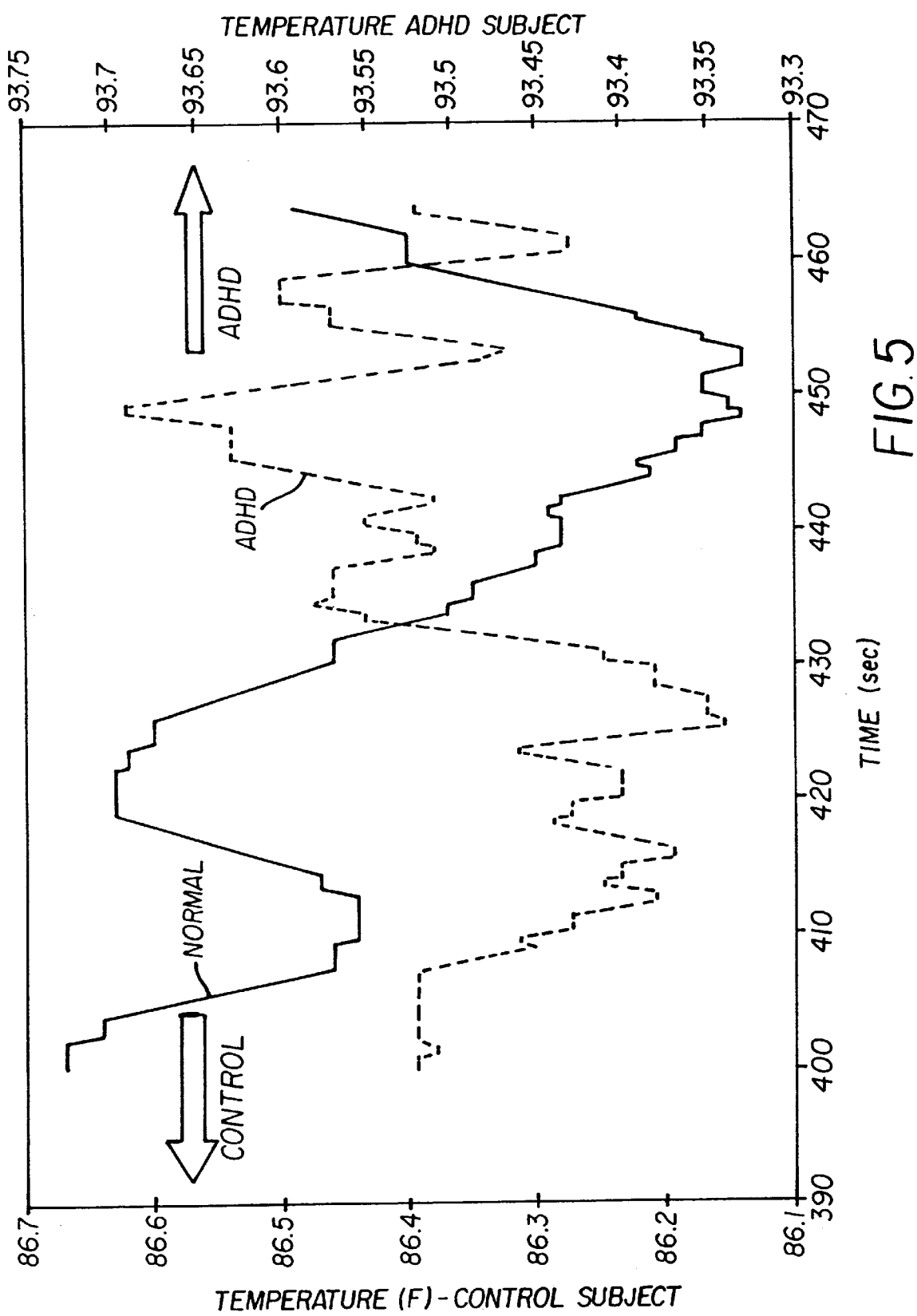
FIGS. 5 and 6 are graphical views useful in explaining the present invention.
Figure 6:
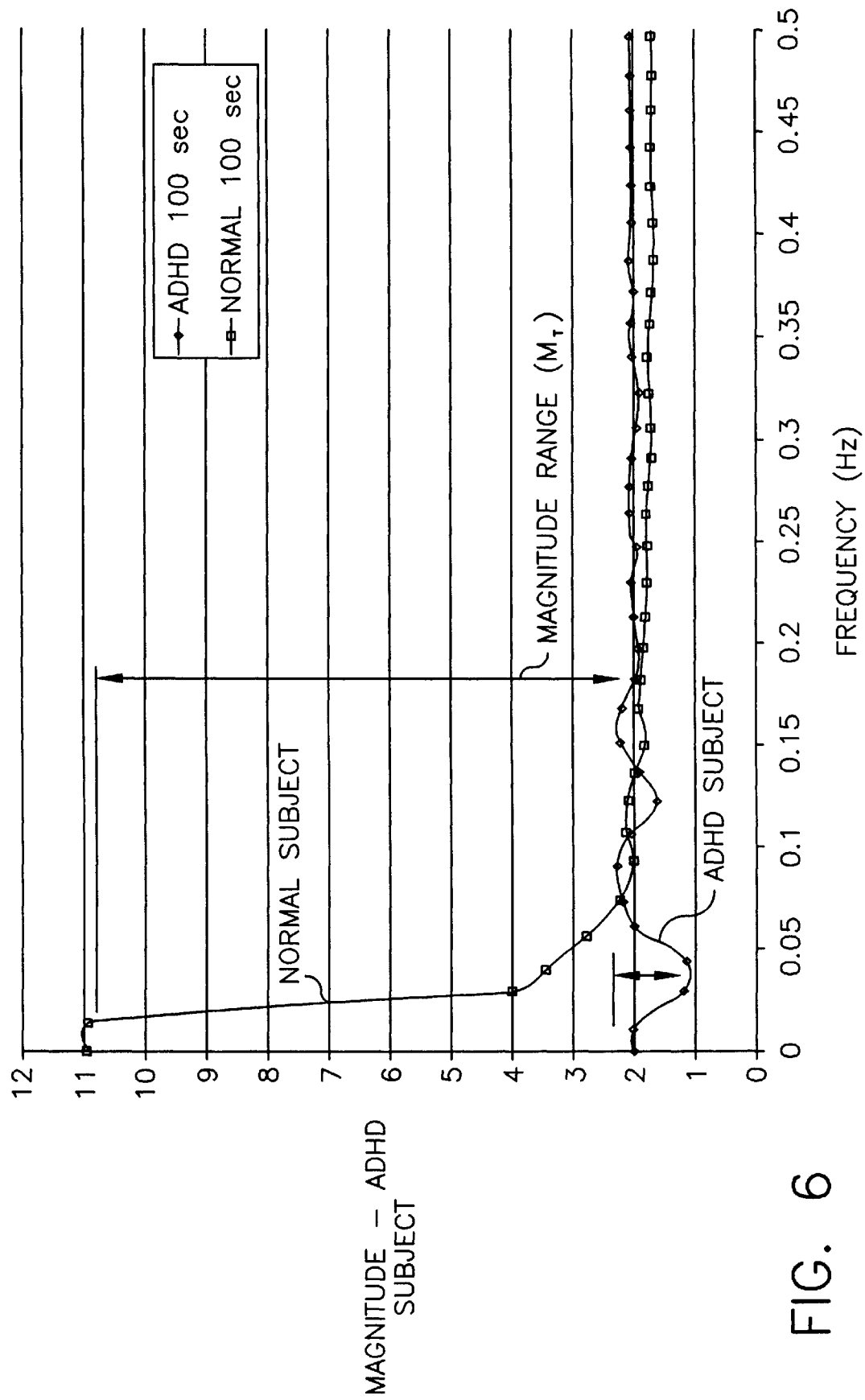

FIG. 5 graphically illustrates the temperature signal during one window for a normal subject and a person diagnosed with ADHD. FIG. 6 graphically illustrates the magnitude transform for the data corresponding with a subject with ADHD and a normal subject. The magnitude spectrum undergoes dramatic changes essentially changing from a hyperbolic curve to a flat response. These graphical illustrations as well as the following can be displayed on display 110 or on some other visual indication device.

The following is another feature of the present invention:
Raw Data
The raw data $T_{i,k}(t)$ is the temperature taken at a fingertip during the baseline period.
Windows
The data for each session were divided into a series of windows prior to performing the Fourier Transform operation. Call the window width w. For each window a FFT algorithm calculates the Fourier Transform F(f). The Magnitude and Phase of this transform are defined as given above. The range of magnitude variation during a window is given below where $f_{max}$ and $f_{min}$ are the frequencies where the Magnitude is the greatest and the least respectively (note the dc component at frequency zero is excluded).

$$M_{range} = [M(f_{max}) - M(f_{min})]$$

Session Mean and Standard Deviation
The mean magnitude range for subject i during session k is found from equation 1.0. where m is the number of windows in the session.

$$\langle M_{i,k} \rangle = \frac{\sum_{j=1}^{m} [M(f_{max})_j - M(f_{min})_j]}{m} \quad (1.0)$$

And the corresponding standard deviation is:

$$\langle s_{i,k} \rangle = \sqrt{\frac{\sum_{j=1}^{m} \{[M(f_{max})_j - M(f_{min})_j] - \langle M_{i,k} \rangle\}^2}{m-1}} \quad (1.1)$$

Figures 7, 8:
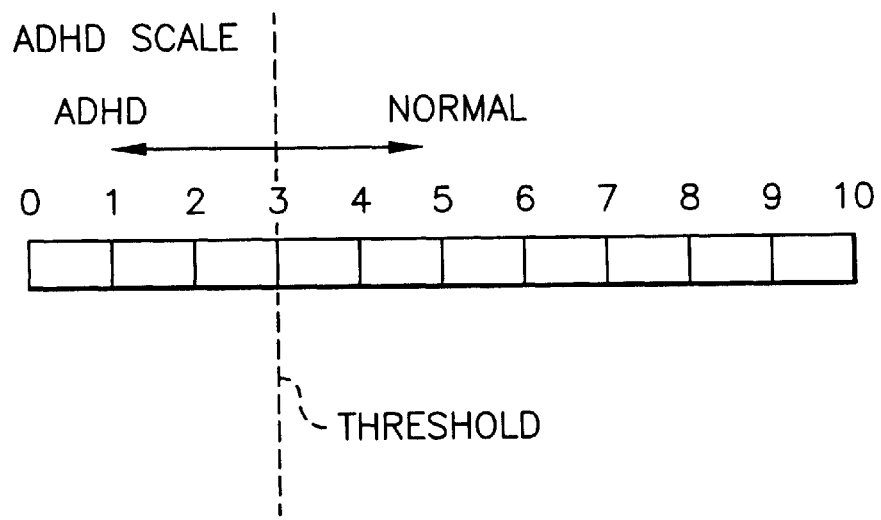
FIG. 7 is a diagrammatic view useful in explaining the present invention.
FIG. 8 is a diagrammatic view useful in explaining the present invention.

Determination Indicator
Positive diagnostic indicator is established based upon the chart of FIG. 7 by setting a threshold level (e.g., 3) for one of the parameters. Below that limit, the subject has a positive diagnostic indicator for ADHD. Above the limit, the subject has a negative diagnostic indicator for ADHD. This procedure can be improved by taking peripheral temperatures during different times of the day over a period of one or more days. FIG. 8 shows the results taken at different times of the day over a period of two days.

Figure 9:
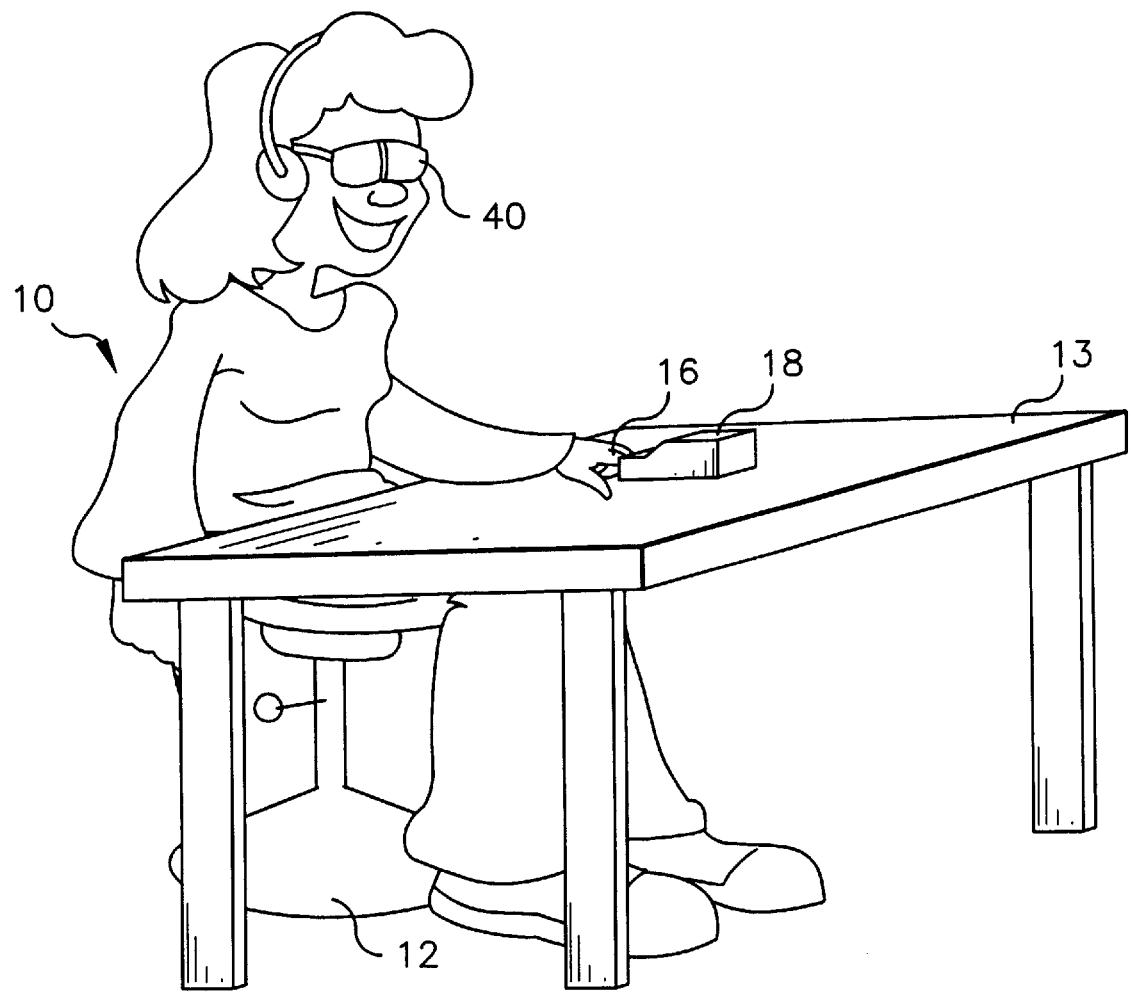
FIG. 9 is a diagrammatic view of another embodiment of the present invention.

FIG. 9 is a diagrammatic view of the subject 10 and the analyzer 18 in another embodiment of the present invention. Shown is the subject 10, wearing a pair of translucent glasses or goggles 40. The glasses or goggles 40 are used to block any visual stimulus from the subject 10. An eye mask can also be used.

Figure 10:
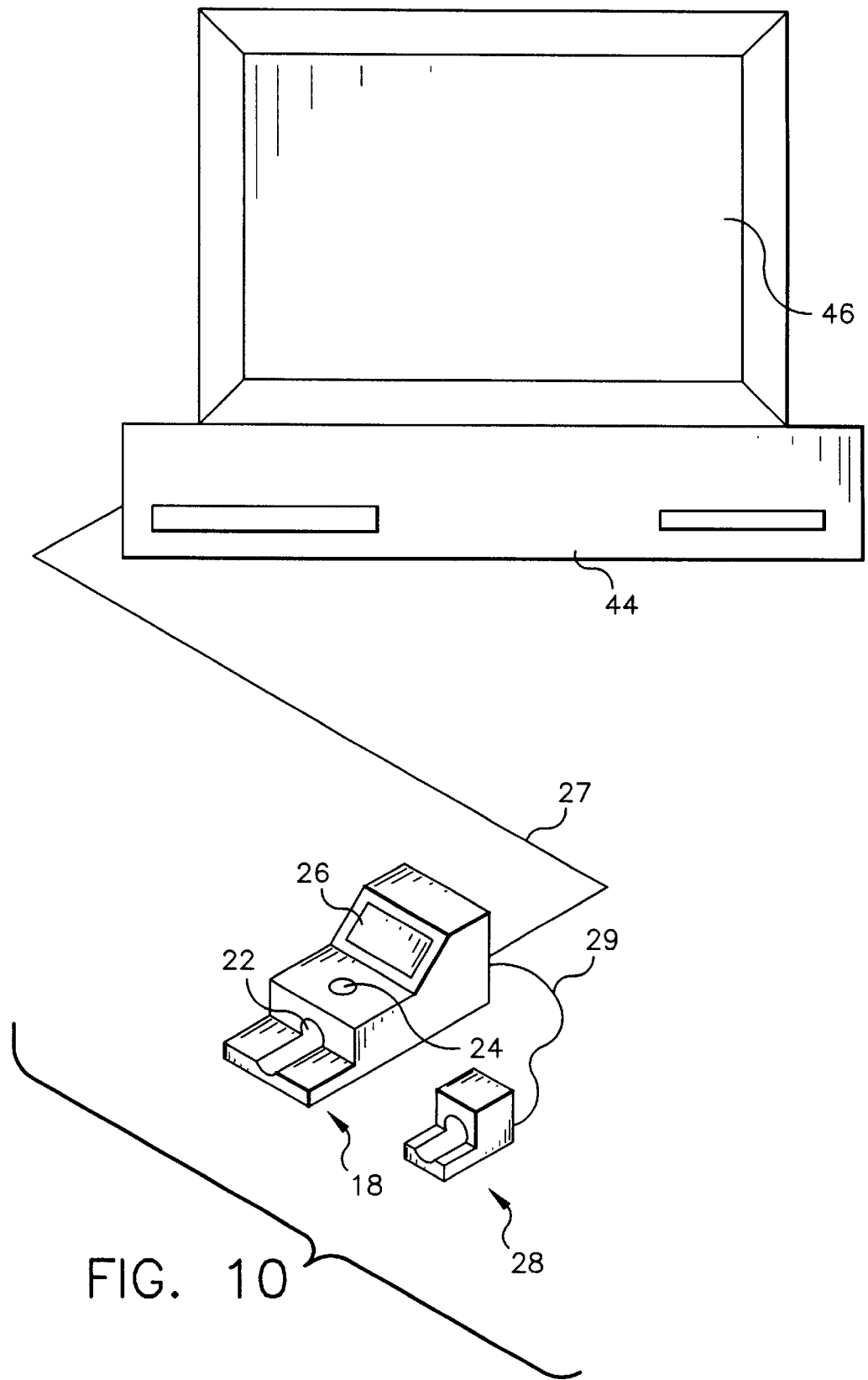
FIG. 10 is a diagrammatic view of another embodiment of the present invention.

A further embodiment of the present invention is shown in FIG. 10. The analyzer 18 is connected via a cable 27 to a computer 44. As in FIGS. 1 and 2 like numerals indicate like parts and operation. The subject's 10 skin temperature response as described above is sampled via the analyzer 18 connected via the cable 27 to the CPU 44. CPU 44 applies the appropriate transforms to analyze the sampled temperatures and displays the results on the monitor 46. The results from the test can be stored in the CPU's memory (not shown) and can be transmitted via a transmission link such as the Internet to other locations. Alternatively the signals from analyzer can be transmitted by wired (telephone) or wireless (cell phone) communication to a remote location where the data is analyzed and transmitted back to analyzer 18 for display.

The invention has been described in detail with particular reference to certain preferred embodiments thereof, but it will be understood that variations and modifications can be effected within the spirit and scope of the invention.

PARTS LIST 10 human subject
12 chair
13 table
14 screen
16 fingertip
17 digit groove
18 analyzer module
20 ear phones
22 sensor
24 on/off switch
26 display
27 cable
28 sensor module
29 cable
30 battery
32 external low voltage power supply port
40 goggles/glasses
44 computer (CPU)
100 analyzer circuit
102 sensor
104 signal conditioner
106 analog to digital converter
108 digital signal analysis
110 LCD display
112 battery
114 power switch
116 power conversion and/or regulation
118 memory card slot

What is claimed is:

1. A kit for determining whether an individual has Attention Deficit Hyperactivity Disorder, comprising;
   a device for sampling the peripheral skin temperature of a human subject during a predetermined time interval when the subject is in an inactive state to produce sampled peripheral skin temperature data; and
   an analyzer for analyzing the sampled peripheral skin temperature data for a pre-selected parameter, to determine whether said pre-selected parameter has a value indicative of ADHD.

2. The kit of claim 1 including a display for displaying said data for said pre-selected parameter to assist in determining whether said pre-selected parameter has a value indicative of ADHD.

3. The kit of claim 1 including earphones for wearing by the subject during said pre-determined time interval to block out ambient noise or to receive white noise to reduce or eliminate audio stimuli from the ambient environment during said time interval.

4. The kit of claim 1 including an eye covering for wearing by the subject to block a visual stimulus from distracting the subject during said predetermined time interval.

5. The kit of claim 1 including a housing for holding said device and said analyzer.

6. The kit of claim 1 wherein said device includes a temperature sensor for sensing the peripheral temperature of at least one finger of said human subject.

7. The kit of claim 1 including a battery for powering said device and said analyzer.

8. The kit of claim 1 including a link for linking said analyzer to a computer.

9. The kit of claim 1 wherein said device includes first and second temperature sensors for sampling the skin temperature in two different peripheral regions of said human subject.

10. The kit of claim 9 wherein said first and second temperature sensors are configured to sample the skin temperature of different fingers of a human subject.

11. The kit of claim 1 wherein said analyzer includes a memory media which is removable.

12. A method of determining whether an individual has Attention Deficit Hyperactivity Disorder (ADHD) using a kit having a device for sampling the peripheral skin temperature of a human subject to produce sampled data and an analyzer for analyzing the sampled data for a pre-selected parameter the method comprising:
   sampling the peripheral skin temperature of a human subject with the device of the kit during a predetermined time interval when the subject is in an inactive state to provide sampled peripheral skin temperature data; and
   using the analyzer of the kit to analyze the sampled peripheral skin temperature data for a pre-selected parameter, to determine whether said pre-selected parameter has a value indicative of ADHD.

13. The method of claim 12 wherein the skin temperature of at least one extremity of a human subject is sampled.

14. The method of claim 12 wherein skin temperature of at least one finger of a human subject is sampled.

15. The method of claim 12 wherein said kit includes earphones and wherein during said predetermined time interval when said subject is in an inactive state, the subject wears said earphones to block out ambient noise or to receive white noise to reduce or eliminate audio stimulus from the ambient environment during said time interval.

16. The method of claim 12 wherein said data is analyzed with a fast fourier transform algorithm to produce frequency and phase data and said phase data is used to determine whether the subject has ADHD.

17. The method of claim 16 wherein said frequency and phase data is processed to produce magnitude range data which is used to determine whether the subject has ADHD.

* * * * *